United States Patent [19]

Yonezawa

[11] Patent Number: 4,770,789
[45] Date of Patent: Sep. 13, 1988

[54] PROCESS OF TREATMENT FOR THE RESIDUE PRODUCED IN PURIFICATION OF INDUSTRIAL PENTACHLOROPHENOL

[75] Inventor: Taiji Yonezawa, Kyoto, Japan

[73] Assignee: Yonezawa Chemical Industry Co., Ltd., Kyoto, Japan

[21] Appl. No.: 869,898

[22] Filed: Jun. 3, 1986

[30] Foreign Application Priority Data

Feb. 13, 1986 [JP] Japan .................................. 61-29598

[51] Int. Cl.$^4$ ........................ B01D 15/00; B01J 20/34
[52] U.S. Cl. .................................... 210/670; 210/694; 502/25; 502/38; 502/514
[58] Field of Search .............. 210/670, 673, 677, 694; 502/421, 423, 436, 514, 25, 38

[56] References Cited

U.S. PATENT DOCUMENTS 2,254,745  9/1941  Jannek ................................. 210/694
3,244,621  4/1966  Bouthilet ............................ 210/694

Primary Examiner—Ivars Cintins
Attorney, Agent, or Firm—Wenderoth, Lind & Ponack

[57] ABSTRACT

A process of treatment for harmful impurity-containing residue produced in the purification of industrial pentachlorophenol, which process is characterized in that said harmful impurities are all rendered harmless by carrying out the following steps:

volatilizing the water and gases adsorbed on the active charcoal in said residue;

heating the above treated residue so that most of the adsorbed materials in said residue are either carbonized or thermally decomposed whereas the rest volatilizes as such together with the thermal decomposition products to be deposited; and treating repeatedly the organic matter thus deposited in the next cycle of the purification in the same manner, or subjecting the matter remaining after heating treatment to decomposition combustion by heating; or heating said organic matter thus deposited in an aqueous solution of sodium hypochlorite so as to dissolve most of it, and treating the insoluble matter formed thereby in the next cycle of the purification in the same manner, or subjecting said insoluble matter to decomposition combustion by heating.

4 Claims, No Drawings

PROCESS OF TREATMENT FOR THE RESIDUE PRODUCED IN PURIFICATION OF INDUSTRIAL PENTACHLOROPHENOL

FIELD OF THE INVENTION

This invention relates to a process of treatment which enables us to treat and eventually to waste in a substantially harmless state the purification residue which is produced in the process of purification for industrial pentachlorophenol, containing harmful impurities such as various kinds of phenolic acid substances and non-phenolic neutral substances.

BACKGROUND OF THE INVENTION

Pentachlorophenol is industrially manufactured by the chlorination of phenol or the hydrolysis of hexachlorobenzene, but it always contains various kinds of phenolic acid substances and non-phenolic neutral substances as impurities.

Since among these impurities, however, there are found chlorodibenzodioxines and chlorodibenzofurans that are known to be strongly poisonous and their so-called precursors such as chlorodiphenyl ethers, chlorophenoxyphenols, and chlorodihydroxybiphenyls, when industrial pentachlorophenol is to be used as an agricultural chemical, it is required to remove the above described poisonous impurities.

In view of the above described situation the present inventor formerly developed a process of purification for industrial pentachlorophenol, which can advantageously remove the above described impurities contained therein (Japanese Patent Application No. 87982/1985).

BRIEF SUMMARY OF THE INVENTION

The object of the invention of the present application is to provide a process of treatment for harmful impurity-containing residue produced in the purification of industrial pentachlorophenol, wherein the sodium salt of said pentachlorophenol is brought into contact with active charcoal in the form of an aqueous solution of said sodium salt so that the harmful impurities present in said solution are adsorbed on said active charcoal to be separated and removed, which process is characterized by that said harmful impurities are all rendered harmless by carrying out the following steps:

(1) maintaining said residue at a temperature below 120° C. under a diminished pressure so as to volatilize the water and gases adsorbed on the active charcoal in said residue;

(2) heating the above treated residue to 600° C. or higher in a heat reaction vessel equipped with a cooling section while maintaining a hermetically sealed state under a diminished pressure so that most of the adsorbed materials in said residue are either carbonized or thermally decomposed whereas the rest volatilizes as such together with the thermal decomposition products to be deposited on the cooling section of said heat reaction vessel; and (3-a) mixing the organic matter thus deposited on the cooling section of said heat reaction vessel together with the residue produced in the corresponding step of the next cycle of the purification to be repeatedly subjected to the treatment heating to 600° C. or higher, or (3-b) heating said organic matter deposited in an aqueous solution of sodium hypochlorite so as to dissolve most of it, and mixing the insoluble matter formed thereby in minute amounts together with the residue produced as above in the next cycle of the purification to be similarly treated, or (4) subjecting said insoluble matter formed in minute amounts in the above (3-b) or, in general, minute amounts of the matter remaining after the above described treatment heating to 600° C. or higher to decomposition combustion by heating to 1,200° C. or higher in an atmosphere of oxygen.

DETAILED DESCRIPTION OF THE PREFERRED EMBODIMENTS OF THE INVENTION

In this invention, it was found that when the residue consisting mainly of the above described impurity-absorbed active charcoal which is produced in the process for purification of the above described pentachlorophenol, wherein an aqueous solution of sodium salt of industrial pentachlorophenol is brought into contact with active charcoal so that the impurities contained in said solution are separated for removal by being adsorbed on said active charcoal, is maintained at a temperature below 120° C. under a diminished pressure of about 100 mmHg so as to volatilize the water and gases adsorbed on the active charcoal in said residue and then further heated to 600° C. or higher in a heat reaction vessel equipped with a cooling section while maintaining a hermetically sealed state under a diminished pressure, the reaction system can always be under a diminished pressure instead of under an increased pressure. The impurities adsorbed on the active charcoal are either carbonized or thermally decomposed though some of them volatilize as such together with the thermal decomposition products to be deposited on the cooled part of the reaction vessel. The active charcoal recovered contains no harmful impurities, restoring the activity that can be used in said purification, so that it can be either wasted without the danger of environmental pollution or reused conveniently.

However, the above described deposited organic matter, which contains harmful impurities, is treated in the following manner.

(1) It is mixed together with the active charcoal residue which is produced in the next cycle of the purification of pentachlorophenol, and again heated to 600° C. or higher under a hermetically sealed condition to perform the second carbonization or thermal decomposition.

(2) Since the deposited organic matter is almost all soluble in a hot solution of sodium hypochlorite, it can be reduced down to a minute quantity by dissolution followed by filtration.

(3) The residue thus reduced to a minute quantity is again mixed with the residue produced in the next cycle of the purification and heated to 600° C. or higher in a hermetically sealed state under a diminished pressure to be carbonized or thermally decomposed.

(4) The residue reduced to a minute quantity is also subjected to combustion decomposition in an atmosphere of oxygen at 1200° C. or higher. In this invention, in accordance with the process disclosed in Japanese Patent Application No. 87982/1985 industrial pentachlorophenol is dissolved in an aqueous solution of a basic substance such as sodium carbonate, potassium carbonate, sodium sulfite, potassium sulfite, etc., and to the resulting solution, in which the impurities remain undissolved, active charcoal is added and stirred to effect the adsorption of said impurities in the solution on said active charcoal, and then, by removing the impurity-adsorbed active charcoal by filtration there is obtained a solution of the salt of pentachlorophenol substantially free from impurities, whereby the active charcoal obtained as the purification residue and containing the above described impurities is taken to be the subject of the treatment in the process of this invention.

In this invention, thus, the active charcoal (hereinafter referred to as purification residue) which contains the impurities and some quantity of sodium salt of pentachlorophenol etc. adsorbed thereon is placed in a reaction vessel, and maintained at a temperature below 120° C., for example, at 100°–120° C., under a diminished pressure, for example, under 120 mmHg. These conditions are intended to prevent the pressure within the reaction vessel from increasing where the water and gases adsorbed in the purification residue volatilize upon the subsequent treatment heating to 600° C. or higher, and also they have been determined taking into consideration the upper and lower rough limit of the treating condition that the water and gases adsorbed on active charcoal almost volatilize, whereas most of the impurities neither thermally decompose nor sublime. By virtue of such a pretreatment, even if the reaction vessel is heated to 600° C. or higher, or preferably to 800° C. in a hermetically sealed state under a diminished pressure such as 120 mmHg, the reaction vessel never becomes a pressurized state, so that the heating can be achieved safely in a hermetically sealed state. By this heating the impurities undergo heating in an oxygen free atmosphere, and most of them are carbonized while some are thermally decomposed and some volatilize as such and deposit on the cooled part of the reaction vessel. After the reaction vessel has cooled and the active charcoal and the deposited material are separately removed. As the active charcoal contains no longer harmful impurities, and has the activity that can be reused in the purification, it may be wasted or reused.

On the other hand, the quantity of the deposited material is extremely small as compared with the impurities present in industrial pentachlorophenol, and the quantity of the gases generating when heated to 800° C. is also such that the reaction vessel never changes to a pressurized state, so that it is considered that what happens upon heating in an oxygen free atmosphere is mainly the carbonization and partially the thermal decomposition of the organic matter and also the volatilization of the thermal decomposition product though some of the organic matter may volatilize as it is.

As the above described deposited material contains harmful impurities, it is mixed with the purification residue produced in the next cycle of the purification and again heated to 800° C. If we could find that even by repeating this operation infinite times the deposited material does not increase in its quantity, it would be the most desirable thing. After three times of repetition there was recognized no tendency of increasing. As the countermeasure for the case where any tendency of increasing should come to pass, investigation was made on the decomposition dissolution by the use of sodium hypochlorite.

The above described deposited material reacts slowly with a hot solution of sodium hypochlorite, and the greater part of it undergoes decomposition dissolution, being converted to harmless impurities. The insoluble residue is found to be in an extremely small amount but still contains harmful impurities. It is advantageous that this extremely small quantity of insoluble matter is mixed with the purification residue produced in the next cycle of the purification and again subjected to heat treatment at 800° C. It is also found that when said insoluble matter is burnt at 1200° C. or higher in an atmosphere of oxygen, it is converted to harmless gases forming no longer any deposit. All the combustion gas was allowed to pass to a benzene trap and the benzene solution was concentrated and then examined by gas chromatography.

EXAMPLE 1

Purification of industrial pentachlorophenol 100 g of industrial pentachlorophenol, 20 g of sodium carbonate, and 800 g of water were heated to 80°–90° C. to give a solution of sodium salt of pentachlorophenol. In the resulting solution there was present a few % of harmful impurities as insoluble matter, but to the solution as it was, there was added 0.5 g of powdery active charcoal and after 30 minutes of stirring the solution was filtered. The pentachlorophenol obtained by acidifying the filtrate contained no harmful impurities.

Treatment of purification residue

The filter cake obtained in the above described purification weighed 2.04 g. The dried cake was placed in the bottom of a ceramic test tube 2 cm in diameter and 20 cm in length, and sucked for 1 hour at 100° C. and 120 mmHg. While maintaining the above described diminished pressure the cock of the suction line was closed to hermetically seal the system. The bottom of the test tube containing the purification residue was heated to 800° C. for 5 minutes. After cooling the active charcoal was recovered by vacuum suction without touching the part near the mouth of the test tube (where the deposited material adhered). The active charcoal weighed 1.14 g, which showed an increase in weight due to the inorganic impurities in the raw material pentachlorophenol. Next, the test tube was washed with benzene and then, with methanol, and the combined liquids were filtered and evaporated to dryness to recover 0.48 g of deposited organic matter.

EXAMPLE 2

Purification of sodium salt of industrial pentachlorophenol

The raw material used in this purification was the product manufactured from pentachlorophenol and sodium carbonate, so that the content of the harmful impurities was small on account of the fact that when the sodium salt was manufactured fractional dissolution was caused by sodium carbonate.

The solution obtained by dissolving 1 kg of sodium salt of pentachlorophenol in 8 kg of water contained 0.3% of insoluble matter, but to the solution as it was, there was added 5 g of active charcoal and after 30 minutes of stirring the solution was filtered. By acidifying the thus obtained filtrate there was obtained pentachlorophenol free from harmful impurities.

Treatment of purification residue 5.32 g of the purification residue produced in the above described purification was heated to 800° C. in a hermetically sealed state under a diminished pressure in the same manner as in Example 1. There were recovered 5.11 g of active charcoal and 0.023 g of deposited material.

EXAMPLE 3

Deposited material was repeatedly mixed with the purification residue in the next cycle of the purification and subjected to the hermetically sealed heat treatment under a diminished pressure to examine whether the weight of the deposited material increases or decreases. The purification and the treatment of the purification residue in Example 2 were repeated three times, in which case 0.031 g of deposited material obtained in the treatment of the purification residue of the first time was mixed with 5.33 g of purification residue of the second time and subjected to the hermetically sealed heat treatment under a diminished pressure, whereby as the deposited material of the second time there was obtained 0.036 g, and similarly as the deposit of the third time there was obtained 0.035 g. Thus, no significant increase in the weight of the deposited material due to the repetition of the above described treatment was recognized.

EXAMPLE 4

Quality of the active charcoal recovered 1 g of active charcoal recovered was extracted with benzene for 8 hours in a Soxhlet's extractor, and the resulting benzene solution was concentrated and analyzed by gas chromatography, but harmful impurities could not be detected.

Using 5 g of active charcoal recovered the purification of sodium salt of pentachlorophenol was carried out as in Example 2. The pentachlorophenol obtained in this way contained no harmful impurities.

EXAMPLE 5

Decomposition dissolution of deposited material by sodium hypochlorite

As in Example 2, 1 kg of sodium salt of pentachlorophenol was purified to give 5.32 g of purification residue, which was heated to 800° C. in a hermetically sealed state under a diminished pressure as in Example 1 to form 0.23 g of volatilized and deposited material. To 0.23 g of this material there was added 100 cc of solution of sodium hypochlorite (effective chlorine 12%) and heated at 70°-80° C. for 4 hours. Almost all the deposited material underwent the decomposition dissolution giving a slightly cloudy solution. When the solution was filtered through a membrane filter of pore size 0.3 micron made of nitrocellulose, there was obtained 0.0002 g of insoluble matter. This quantity is as small as $10^{-8}$ per 1 kg of sodium salt of pentachlorophenol before the purification, but contains harmful impurities.

EXAMPLE 6

Treatment of the insoluble matter in sodium hypochlorite treatment

Although it is advantageous that the above described insoluble matter in the sodium hypochlorite treatment is mixed with the purification residue produced in the next cycle of the purification and again subjected to the hermetically sealed heat treatment under a diminished pressure at 800° C., the quantity is as small as 2 g per 100 t of pentachlorophenol as the raw material, so that it is also possible to treat completely according to the analytical method.

0.0002 g of the insoluble matter in the sodium hypochlorite treatment obtained in Example 5 was burnt in a combustion tube which is in common use to burn a substance in excess oxygen at 1200° C. for the quantitative determination of carbon and sulfur in iron and steel. All the combustion gas was allowed to pass to benzene trap, and the benzene solution was concentrated and the harmful impurities were examined by gas chromatography, but could not be detected, and after the evaporation of the benzene no residue was left.

In the above described investigation the detection of the harmful impurities, chlorodibenzodioxin, chlorodibenzofuran, ect. was resorted to G-3800 non-radiation type apparatus for gas chromatography, equipped with an electron capture detector, manufactured by Yanagimoto Seisakusyo (column length 20 m, liquid phase silicone OV-101).

What is claimed is:

1. In a process for the treatment of harmful impurity-containing residue produced in the purification of industrial pentachlorophenol, wherein an aqueous solution of a sodium salt of said pentachlorophenol is brought into contact with active charcoal so that water, volatilizable gases and harmful impurities, which comprise chlorodibenodioxines, chlorodibenzofurans, and precursors thereof, said precursors being chlorodiphenyl ethers, chlorophenoxy phenols, and chlorodihydroxybiphenyls, are adsorbed on said active charcoal, the solution of the sodium salt of pentachlorophenol is recovered, and the impurities are separated from the active charcoal and disposed of the improvement which comprises
    (1) volatilizing the adsorbed water and gases by heating the charcoal having adsorbed water, volatilizable gases and impurities at a temperature below 120° C. and under diminished pressure for a time sufficient to volatilize the adsorbed water and volatilizable gases;
    (2) thereafter heating the charcoal with adsorbed impurities to 600° C. or higher in a heat reaction vessel equipped with a cooling section while maintaining a hermetically sealed state under a diminished pressure so that the adsorbed impurities are either carbonized, thermally decomposed or volatilized, with the thermally decomposed products, and the volatilized products being deposited on the cooling section of the heat reaction vessel; and
    (3) recycling the matter deposited on the cooling section of the heat reaction vessel to step 2 of this process.

2. The process according to claim 1, wherein the material deposited on the cooling section of the heat reaction vessel is subjected to a decomposition combustion treatment at a temperature of at least 1200° C. in an atmosphere of oxygen, and harmless gases are vented to the atmosphere.

3. The process according to claim 1, wherein the material deposited on the cooling section of the heat reaction vessel is heated in an aqueous solution of sodium hypochlorite and the insoluble matter thereby formed is recycled to step 2 of this process.

4. The process according to claim 3, wherein the insoluble matter formed during the dissolution in an aqueous solution of sodium hypochlorite is subjected to decomposition combustion by heating to at least 1200° C. in an atmosphere of oxygen.

* * * * *